US009500605B2

(12) United States Patent
Lingren et al.

(10) Patent No.: US 9,500,605 B2
(45) Date of Patent: Nov. 22, 2016

(54) PROMPT GAMMA NEUTRON ACTIVATION SUBSTANCE ANALYZERS

(71) Applicant: Sabia Inc., San Diego, CA (US)

(72) Inventors: Clinton LaMar Lingren, San Diego, CA (US); Abhinandan Sheshadri, San Diego, CA (US); James Francis Miller, Solana Beach, CA (US); Thomas Charles Dannemiller, Carlsbad, CA (US); Stephen James Foster, Vista, CA (US); Nichelle Diane Worthington, San Diego, CA (US); Bradley Allen Moyer, San Diego, CA (US)

(73) Assignee: Sabia Inc., San Diego, CA (US)

( * ) Notice: Subject to any disclaimer, the term of this patent is extended or adjusted under 35 U.S.C. 154(b) by 0 days.

(21) Appl. No.: 15/059,183

(22) Filed: Mar. 2, 2016

(65) Prior Publication Data

US 2016/0178542 A1 Jun. 23, 2016

Related U.S. Application Data

(63) Continuation of application No. 14/329,373, filed on Jul. 11, 2014, now Pat. No. 9,291,580.

(51) Int. Cl.
*G01T 1/20* (2006.01)
*G01N 23/09* (2006.01)
*G01N 23/222* (2006.01)
*G01T 3/06* (2006.01)

(52) U.S. Cl.
CPC ............ *G01N 23/222* (2013.01); *G01N 23/09* (2013.01); *G01T 1/2006* (2013.01); *G01T 1/2018* (2013.01); *G01T 3/06* (2013.01)

(58) Field of Classification Search
CPC .............................. G01N 23/09; G01T 1/2006
See application file for complete search history.

(56) References Cited

U.S. PATENT DOCUMENTS

| 2,874,611 | A | 2/1959 | Luboshez |
| 4,171,485 | A | 10/1979 | Marshall |
| 4,582,992 | A | 4/1986 | Atwell |
| 4,694,165 | A | 9/1987 | Proctor |
| 6,157,034 | A | 12/2000 | Griebel |

(Continued)

OTHER PUBLICATIONS

Leetham, "Online Stockpile Analysis", : http://www.thermoscientific.com/content/dam/tfs/ATG/CAD/CAD%20Documents/Third-Party%20Papers/Cement,%20Coal,%20Minerals%20Sampling%20and%20Online%20Analysis/Cement%20Online%20Elemental%20Analyzers/D00459~.pdf, World Cement, Jan. 2008.

(Continued)

*Primary Examiner* — Mark R Gaworecki
(74) *Attorney, Agent, or Firm* — Fish & Richardson, P.C.

(57) ABSTRACT

Methods and systems are provided to improve prompt gamma neutron activation substance analyzers. In one aspect, a detector unit for prompt gamma neutron activation analysis includes: a scintillator configured to fluoresce when impacted by gamma rays generated by absorption of neutrons by a substance to be analyzed; a photosensor configured to receive fluorescence from the scintillator; electronics coupled with the photosensor, the electronics configured to receive and process analog signals from the photosensor and output digital detection signals for the substance; and a housing containing the scintillator, the photosensor, and the electronics; wherein the housing includes interfaces configured to receive cables capable of providing power, temperature control, and digital communication signals.

23 Claims, 4 Drawing Sheets

(56) References Cited

U.S. PATENT DOCUMENTS

| | | |
|---|---|---|
| 6,396,061 B1 | 5/2002 | Madden |
| 7,152,002 B2 | 12/2006 | Lingren |
| 7,778,783 B2 | 8/2010 | Lingren |
| 8,426,821 B2 | 4/2013 | Harris |
| 2003/0225531 A1 | 12/2003 | Lingren |
| 2007/0029493 A1 | 2/2007 | Kniss |

OTHER PUBLICATIONS

Leetham, "PGNAA Improves Process and Quality Control in Cement Production", http://acceleratingscience.com/mining/pgnaa-improves-process-and-quality-control-in-cement-production/, Jun. 17, 2014.

"Neutron Elemental Analysis", SODERN, http://www.sodern.com/sites/en/refiNeutron-elemental-analysis_33.html, Jun. 20, 2014.

Registry of Radioactive Sealed Sources and Devices, http://www.nrc.gov/, No. GA-0716-D-101-S, Mar. 20, 1986.

Registry of Radioactive Sealed Sources and Devices, http://www.nrc.gov/, No. CA-305-D-103-S, Apr. 20, 1993.

Registry of Radioactive Sealed Sources and Devices, http://www.nrc.gov/, No. GA-0716-D-103-S, May 8, 2001.

Registry of Radioactive Sealed Sources and Devices, http://www.nrc.gov/, No. CA-1045-D-101-B, Oct. 10, 2007.

Registry of Radioactive Sealed Sources and Devices, http://www.nrc.gov/, No. CA-0305-D-101-S, Oct. 22, 2007.

Registry of Radioactive Sealed Sources and Devices, http://www.nrc.gov/, No. CA-0305-D-104-S, Oct. 22, 2007.

Registry of Radioactive Sealed Sources and Devices, http://www.nrc.gov/, No. CA-0305-D-105-S, Oct. 22, 2007.

"Thermo Fisher Scientific Launches New PGNAA Slurry Analyzer", http://www.mining.com/web/thermo/fisher-scientific-launches-new-pgnaa-slurry-analyzer/, Oct. 30, 2012.

Invitation to Pay Additional Fees, International Application No. PCT/US2015/036085, mailed Aug. 17, 2015, 2 pages.

International Search Report and Written Opinion in International Application No. PCT/US2015/036085, dated Nov. 9, 2015, 15 pages.

Decision on Protest in International Application No. PCT/US2015/036085, dated Nov. 13, 2015, 2 pages.

Response to Invitation to Pay Additional Fees in International Application No. PCT/US2015/036085, filed Sep. 16, 2015, 4 pages.

PROMPT GAMMA NEUTRON ACTIVATION SUBSTANCE ANALYZERS

CROSS-REFERENCE TO RELATED APPLICATIONS

This application is a continuation application of, and claims priority to, U.S. patent application Ser. No. 14/329,373, entitled PROMPT GAMMA NEUTRON ACTIVATION SUBSTANCE ANALYZERS, which was filed on Jul. 11, 2014, and was published as US Pat. Pub. No. 20160011126; this prior application is incorporated by reference in its entirety.

BACKGROUND

This specification relates to substance analyzers, and more particularly, to a bulk substance analyzer unit that can determine the compositional elements of bulk materials using one or more neutron sources and one or more radiation detectors.

When an atom absorbs a neutron, it increases in atomic weight, but at that moment, the chemical properties of the atom do not change, thus forming a new isotope of the same element. When a neutron is absorbed, the absorbing atom emits one or more gamma rays, the number and energies of which are unique to that element. The new isotope may be unstable and seek stability by emitting one or more forms of radiation over a period of time, which may also result in the atom changing to a different element. Every radioactive isotope has a characteristic half-life as it decays to a stable state. An element that has absorbed a neutron can be identified by either the absorption gamma rays that it emits or by the decay-radiation it emits. The latter is normally referred to as neutron activation analysis and the former is often called Prompt-Gamma, Neutron Activation Analysis (PGNAA).

Commercial PGNAA analyzers were introduced during the 1970s and 1980s. PGNAA can measure material composition throughout a relatively large volume of material because neutrons penetrate matter to a great depth and the resulting prompt gamma rays are of energies high enough to permit them to escape from a substantial depth within the material. When the bulk material is bombarded with the neutron radiation, different characteristic gamma-ray energy spectra are produced from different elements in the bulk material. By processing detected signals indicative of gamma ray energies, a measurement can be made regarding the elemental content of the bulk material. Directing a PGNAA analyzer at a stream of industrial material can allow the full stream to be analyzed and an accurate assessment of the composition of bulk materials can be provided quickly, without special processing of the materials. For further details regarding PGNAA analyzer, see U.S. Pat. Nos. 7,152,002 and 7,778,783, which describe improvements for substance analyzers using Prompt Gamma Neutron Activation Analysis for identifying characteristics of a substance; these patents are hereby incorporated by reference in their entirety.

SUMMARY

This specification describes technologies relating to substance analyzers, and more particularly, to a bulk substance analyzer unit that can determine the compositional elements of bulk materials using one or more neutron sources and one or more radiation detectors.

One or more aspects of the subject matter described in this specification can be embodied in a substance analyzer unit that includes a source of neutrons, an opening arranged with respect to the source of neutrons to receive a substance, and a detector assembly including integrated detector units, wherein each of the integrated detector units has a same size and includes a scintillator configured to fluoresce when impacted by gamma rays generated by absorption of neutrons by the substance to be analyzed, a photosensor configured to receive fluorescence from the scintillator, electronics coupled with the photosensor and configured to receive and process analog signals from the photosensor and output digital detection signals for the substance, a housing containing the scintillator, the photosensor, and the electronics, wherein the housing includes interfaces configured to receive cables capable of providing power, temperature control, and digital communication signals, and a handle for ease of installation in and removal from the detector assembly. One or more aspects of the subject matter described in this specification can also be embodied in a system that includes the above substance analyzer unit and one or more additional substance analyzer units, each including a respective source of neutrons, opening, and detector assembly, wherein the source of neutrons and the opening are arranged differently for each of the substance analyzer units.

These and other embodiments can optionally include one or more of the following features. Three or more analyzer units installed at a site can have two or more different configurations. For example, a first of the substance analyzer units can be configured and arranged to handle bulk materials delivered to the first substance analyzer unit by a conveyor belt, a second of the substance analyzer units can be configured and arranged to handle materials delivered in a container that is inserted into the second substance analyzer unit, and a third of the substance analyzer units can be configured and arranged to handle materials delivered to the third substance analyzer unit in a slurry pipe. Moreover, the same analyzer unit configuration can be used for more than one analyzer unit at the same site.

The same size integrated detector units can each include a handle for ease of installation in and removal from the detector assembly of the substance analyzer unit, regardless of its configuration. The substance analyzer unit can be a bulk substance analyzer, the source of neutrons can be an isotopic radioactive source having associated material configured and arranged with respect to the radioactive source to condition emitted neutrons, and the opening can include a channel arranged to carry the substance by the isotopic radioactive source. The detector housing can be made primarily of carbon, hydrogen and oxygen elements, which contribute lower signals to background spectra than other elements when impacted by neutrons. For example, the detector housing can include corrugated plastic configured and arranged to provide thermal insulation and mechanical support for the detector. In addition, the corrugated plastic can include corrugated plastic sheets including polypropylene, polycarbonate, or similar plastics.

The detector assembly can include a detector interface communications module coupled with each of the integrated detector units, and a temperature-control module coupled with each of the integrated detector units. The temperature-control module can also be a power-supply module that includes an AC (alternating current) power input interface and provides power to the detector interface communications module.

In some cases, the interfaces are only two interfaces in the detector housing and one of the only two interfaces is a USB (Universal Serial Bus) interface configured to receive a USB cable from the detector interface communications module to provide both the power and the digital communication signals. Each of the integrated detector units can also include a source of high voltage coupled with the photosensor, and a pre-amplifier coupled with the photosensor, wherein the electronics include an analog to digital converter (ADC) and a controller. The electronics can include a communications module. The communications module can include a wireless communications transceiver configured to send and receive digital data over a wireless network. The controller can include a digital computer including: a bus interface; a hardware processor coupled with the bus interface; memory coupled with the bus interface; an input/output (I/O) interface coupled with the bus interface; and one or more expansion ports coupled with the bus interface.

The detector interface communications module can include interface ports for four or more integrated detector units and can be configured to output digital data for the integrated detector units to a computer network. The detector interface communications module can include, or be coupled with, a wireless communications transceiver, and the computer network can be a wireless network.

The substance analyzer unit can include a renewable energy source and a battery system to provide power for operation of the substance analyzer unit. The renewable energy source can be a solar panel integrated into the substance analyzer unit, and the wireless communications transceiver can be a WiFi transceiver. In addition, the opening can be a passage sized to receive a container that is inserted into the substance analyzer unit and subsequently withdrawn from the substance analyzer unit after analysis steps have been performed, where the container holds the substance being analyzed. For example, the passage can be sized to receive the container from a first side of the passage and eject the container from a second side of the passage.

According to another aspect of the subject matter described in this specification, a detector unit for prompt gamma neutron activation analysis includes: a scintillator configured to fluoresce when impacted by gamma rays generated by absorption of neutrons by a substance to be analyzed; a photosensor configured to receive fluorescence from the scintillator; electronics coupled with the photosensor, the electronics configured to receive and process analog signals from the photosensor and output digital detection signals for the substance; and a housing containing the scintillator, the photosensor, and the electronics; wherein the housing includes interfaces configured to receive cables capable of providing power, temperature control, and digital communication signals. The housing can also include corrugated plastic configured and arranged to provide thermal insulation and mechanical support for the detector unit. Further, the detector unit can include a handle for ease of installation in and removal from a substance analyzer unit. These and other embodiments can optionally include one or more of the following features.

The housing can be made substantially of carbon, hydrogen and oxygen elements, which contribute lower signals to background spectra than other elements when impacted by neutrons. The corrugated plastic can include corrugated plastic sheets including polypropylene, polycarbonate, or similar plastics. Moreover, the detector unit can include: a source of high voltage coupled with the photosensor; and a pre-amplifier coupled with the photosensor; wherein the electronics include an analog to digital converter (ADC) and a controller In some cases, the interfaces are only two interfaces in the housing, and one of the only two interfaces can be a USB (Universal Serial Bus) interface configured to receive a USB cable to provide both the power and the digital communication signals. Further, the electronics can include a communications module.

The communications module can include a wireless communications transceiver configured to send and receive digital data over a wireless network. Further, the controller can include a digital computer including: a bus interface; a hardware processor coupled with the bus interface; memory coupled with the bus interface; an input/output (I/O) interface coupled with the bus interface; and one or more expansion ports coupled with the bus interface.

Particular embodiments of the subject matter described in this specification can be implemented to realize one or more of the following advantages. Background spectra from neutrons being absorbed by materials other than the substance being analyzed can be reduced. Eliminating from the detector housing various types of materials that emit background gamma rays induced by neutrons can result in fewer undesired gamma rays reaching the detector. This can be accomplished while still providing the thermal insulation and mechanical strength needed for protecting the large-mass detector.

Further, the impact of such background spectra on the analysis process can be reduced by reducing the distance that an analog detection signal travels before being processed into the digital domain. Cables that carry an analog signal to detector electronics mounted remotely (e.g., mounted to the side or top of the analyzer, or installed in a separate enclosure or building) need not be used, and thus the added expense of shielded cables to carry low-level signals from the detectors is not needed, and a separate enclosure or building for mounting such electronics is not needed. In addition to improvement in detection analysis from reduction of background spectra and/or elimination of interfering signals, ease of installation, calibration, and maintenance for an analyzer unit can also be improved.

An analyzer unit can be built so as to reduce or eliminate the cables (shielded or otherwise) hooked up to the analyzer. In some cases, only two cables connect to the analyzer unit: a source of electrical power, and a digital communication cable. These two cables can also be eliminated by using solar power and wireless communications. Eliminating cables from the detector to any electronics systems outside the detector can eliminate cables that could pick up electrical noise that would impact performance or could be severed by activities in the vicinity of those cables and result in interruption of analyzer operation. Eliminating cables can significantly reduce the time and cost of installation and can reduce maintenance costs because there are fewer items to fail.

According to one or more additional embodiments of the subject matter described in this specification, an analyzer unit can be designed to provide efficient installation and maintenance for various applications. For example, an analyzer unit can be designed to wrap around a main-stream slurry pipe to facilitate inclusion in a production line. This can avoid the need to use a complex manifold to sample a slurry stream to be brought into the analyzer for analysis. The contents of the main-stream slurry pipe can be quickly analyzed without needing to circulate a sample through the analyzer until an adequate measurement has been obtained. Moreover, greater accuracy and greater process control can be obtained by continuously measuring the full stream of a slurry.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
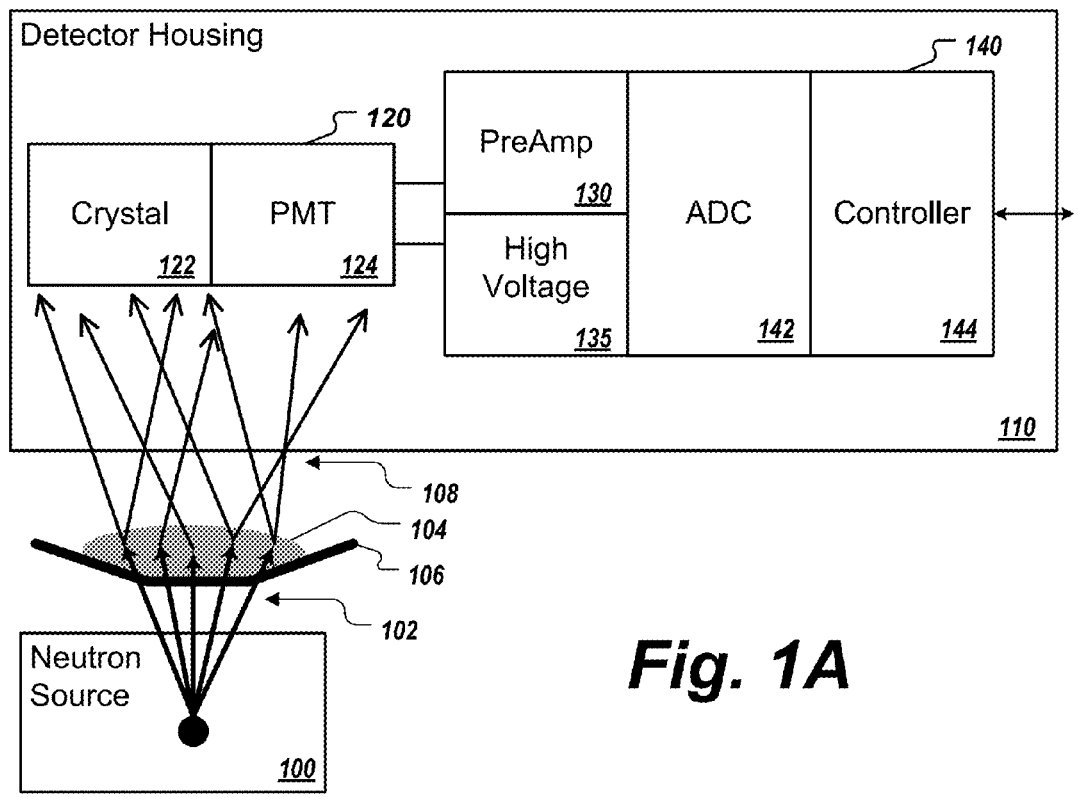
FIG. 1A shows an example of a gamma-ray detector architecture for use with PGNAA.

FIG. 1A shows a gamma-ray detector architecture for use with Prompt-Gamma, Neutron Activation Analysis (PGNAA). A neutron source 100 provides neutrons 102 to impact a substance 104 to be analyzed, which can be carried on a conveyor belt 106 through a channel (as shown), by a slurry pipe, in a sample stream, or in sample containers. The neutron source 100 can be one or more neutron sources, which can be isotopic neutron sources or electric neutron sources. An electric neutron source can include an electrically powered neutron generator. Electronic neutron generators emit neutrons by means of compact linear accelerators, which produce neutrons by fusing isotopes of hydrogen together. The energies of the neutrons can range from about 2.4 MeV to 14 MeV depending on which isotopes are used. The emission of neutrons is terminated by removing the source of electric power from the generator. An isotopic neutron source can include a radioactive material that emits neutrons 102 and containing material around the radioactive material that conditions (and potentially focuses) emitted neutrons 102 to bombard the substance 104. In any case, when the neutrons 102 impact the substance 104 to be analyzed, prompt gamma-rays 108 are generated.

One or more gamma-ray detectors are mounted on an opposite side of the substance 104 from the neutron source 100 to detect the gamma-rays 108 and process the signals thus generated. A detector housing 110 includes a detector 120 that identifies gamma-rays 108 that pass through it. The detector 120 can include a crystal 122 (or other scintillator) and PMT (Photomultiplier) 124 (or other photosensor). The detector 120 can receive a high excitation voltage from a source 135, which can generate a needed high voltage for detection in the detector housing 110. The signals generated by the detector 120 can be amplified by a pre-amplifier 130 and then further processed by electronics 140 for determining which elements absorbed the neutrons and emitted the detected prompt gamma rays.

The electronics 140 are configured to receive and process analog signals from the detector and output digital detection signals. In some implementations, the electronics 140 can be used for controlling the detector 120 and for receiving and processing the signals from the detector 120 and providing communications to systems that may use the analyzer outputs. The electronics 140 can control the excitation of the detector and condition the signal from the detector. The electronics 140 can include circuitry and computer hardware and software for controlling the detector 120 and conditioning and processing the signal to extract the desired information about the material being analyzed and for communicating that information to another device (e.g., a device on the network) where it can be further processed and formatted to satisfy the needs of the particular application.

The electronics 140 can be implemented using special purpose circuitry, general purpose programmable circuitry, field-programmable circuitry, or combinations of these. In some implementations, the electronics 140 include an analog to digital converter (ADC) 142 and a controller 144 that operates in the digital domain. In some implementations, the ADC 142 can be an ADC and DAC (digital to analog converter) chip. The controller 144 can be a computer, which includes computer hardware, plus firmware, software, or both. In some implementations, the controller 144 includes a multichannel analyzer and analysis software. Further, in some implementations, the controller 144 includes the ADC 142.

Figure 1B:
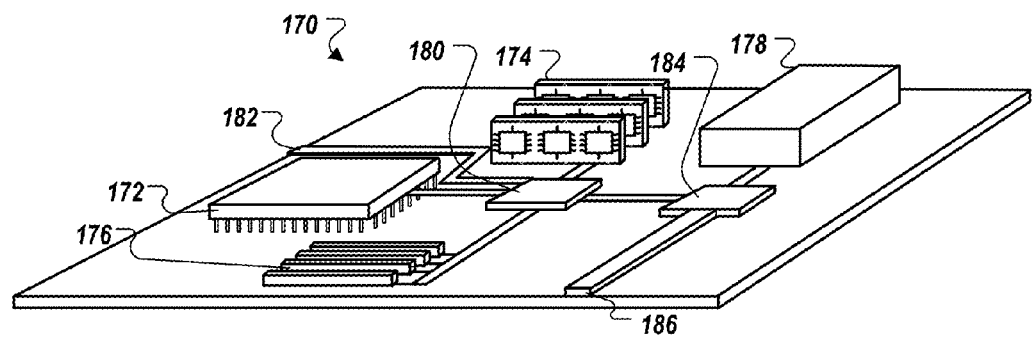
FIG. 1B shows an example of a computer architecture that can be used in the detector architecture of FIG. 1A.

FIG. 1B shows a computer architecture that can be used in the detector architecture of FIG. 1A. A computing device 170 is a digital computer that includes a hardware processor 172, memory 174, a bus interface 180 (e.g., a parallel or serial interface), and an input/output (I/O) interface 182. The computing device 170 can include an ADC and DAC chip, such as AD7985 or AD5791, available from Analog Devices Inc., of Norwood, Mass. The memory 174 can include volatile memory, non-volatile memory, or both. For example, the memory 174 can hold firmware instructions that are run by the hardware processor 172 to perform the functions of the electronics 140. In some implementations, the bus interface 180 is a high-speed interface, and the computing device 170 can include a low speed bus interface 184 to connect with a storage device 178 (e.g., a hard disk drive or solid state memory device). The storage device 178 can include software that is loaded into memory 174 and is run by the hardware processor 172 to perform the functions of the electronics 140. As will be appreciated, the memory 174 and the storage device 178 are examples of a computer-readable medium, which is described further below. Moreover, in some implementations, the computing device 170 can include one or more high-speed expansion ports 176 and one or more low-speed expansion ports 186.

FIG. 1B represents some examples of implementations, but as will be appreciated in view of this disclosure, well known electronics micro-miniaturizing techniques can be used to miniaturize the traditional electronics associated with a PGNAA analyzer. Referring again to FIG. 1A, in various implementations, the introduction of such micro-processing capabilities can result in a full integration of the electronics into the housing of the detector, such that no analog signals enter or exit the detector housing 110, thus reducing (if not eliminating) the possibility of electromagnetic pickup adding to the background spectra of the analyzer. This can be extremely important in as much as such pickup may not be constant in magnitude nor frequency and, therefore, cannot traditionally be eliminated by common subtraction techniques. When the detector electronics are integrated into the detector housing 110, it becomes an integrated detector 110, where only digital signals need enter or exit the detector housing 110.

A source of low-Voltage direct current can be provided to the integrated detector 110, from which the circuitry inside the detector housing 110 generates excitation Voltage sources for circuitry and sensor. A temperature control cable that can be isolated from detection signals can also be brought to the detector housing 110 for ensuring proper detector temperature. Moreover, since at least the initial analysis processing occurs within the confines of the detector housing 110, the data signal output from the detector housing 110 can be an entirely digital signal. PGNAA uses a source of neutrons to induce a gamma-ray signal from the atoms within the material being analyzed. Because each element emits its own characteristic prompt-gamma-ray spectrum when it absorbs a neutron, the total spectrum of all of the gamma rays emitted from the material being tested can be de-convolved to determine the total amount of each element in that material. However, neutron sources emit neutrons in all directions, and those neutrons are then absorbed by all materials in the vicinity. The gamma-ray signals that are emitted from the analyzer and the supporting structure around the analyzer create background spectra from which the spectra of the material being analyzed must be extracted. The quality of the PGNAA measurements is highly affected by the magnitude of the background spectra.

Due to the design of the detector housing 110, no analog signals from the detector 120 need be routed outside of the detector housing 110. This can provide increased flexibility and ease of set up for on-site installations (e.g., at an industrial site) as well as improve performance by reducing the risk of interference on analog data lines (e.g., from electromagnetic interference) that might need to travel some distance outside the detector housing to reach an initial data processing stage. Moreover, to further improve performance, a substantial portion of the detector housing 110 can be constructed from carbon, hydrogen and oxygen elements, which contribute lower signals to background spectra than other elements when impacted by neutrons (e.g., more than 30%, more than 40%, more than 50%, or more than 60% by mass of all elements used to construct the housing). The use of other materials (e.g., aluminum) can be reduced or eliminated. In some implementations, the detector housing 110 can be made primarily of carbon, hydrogen and oxygen elements (e.g., more than 70%, more than 80%, more than 90%, or more than 95% by mass of all elements used to construct the housing).

Figure 2:
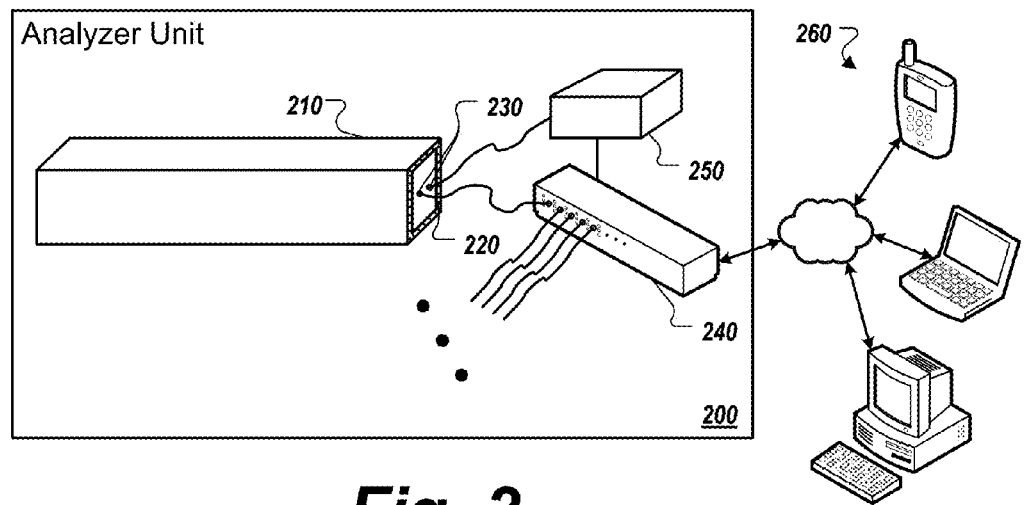
FIG. 2 shows an example of a substance analyzer unit.

FIG. 2 shows an example of a substance analyzer unit 200. The substance analyzer unit 200 includes one or more detector housings 210, such as described above in connection with FIG. 1A. Each detector housing 210 can include corrugated plastic 220 configured and arranged to provide thermal insulation and mechanical support for the detector inside the housing 210. The corrugated plastic 220 can be corrugated plastic sheets made with polypropylene, polycarbonate, or similar plastics. Note that the use of corrugated plastic 220 can provide any needed structural integrity to protect the fragile detectors, but without the additional generation of background spectra as is the case when metal is used for the housing. Thus, materials that might contribute to background spectra (e.g., aluminum or iron) can be reduced or eliminated from the detector housing 210. And in addition to the type of material used for the structure of the detector housing 210, the use of corrugated materials allow a reduction in the amount of the material used to get the required strength for the housing. By these two methods background spectra from the detector housing can be minimized.

In addition, in some implementations, the detector housing 210 provides limited outlets or holes, such that only power, temperature control, and digital communication signals pass through the detector housing 210. For example, the analyzer unit 200 can include a detector interface communications module 240 and a temperature-control module 250 that each couple with each integrated detector 210 through interfaces 230. In some implementations, the temperature-control module 250 can also be a power-supply module that includes an AC (alternating current) power input interface and provides power to the detector interface communications module 240. The module 250 can receive a source of power, such as 120 V AC, and the module 250 can convert this power into a DC Voltage that can be used by the module 240 and the detector(s) 210.

In addition, the modules 240, 250 can have multiple ports for connecting detectors, thus allowing the same modules 240, 250 to be used in different installations with different numbers of detectors. The module 250 can provide a cable to each detector housing 210 for controlling detector temperature. Further, the module 240 can receive the low-Voltage power from the module 250 and control the communications between the integrated detector 210 and a server at some location outside the analyzer unit 200. Thus, the module 240 can include communication technology (e.g., wireless technology such as a WiFi transceiver, or wired technology such as an Ethernet Medium Access Control (MAC) unit) used to communicate with multiple computing devices 260 over a network. One or more of the additional computing devices 260 can be used for display and monitoring, administrative control, additional signal analysis, or a combination of these.

Figure 3:
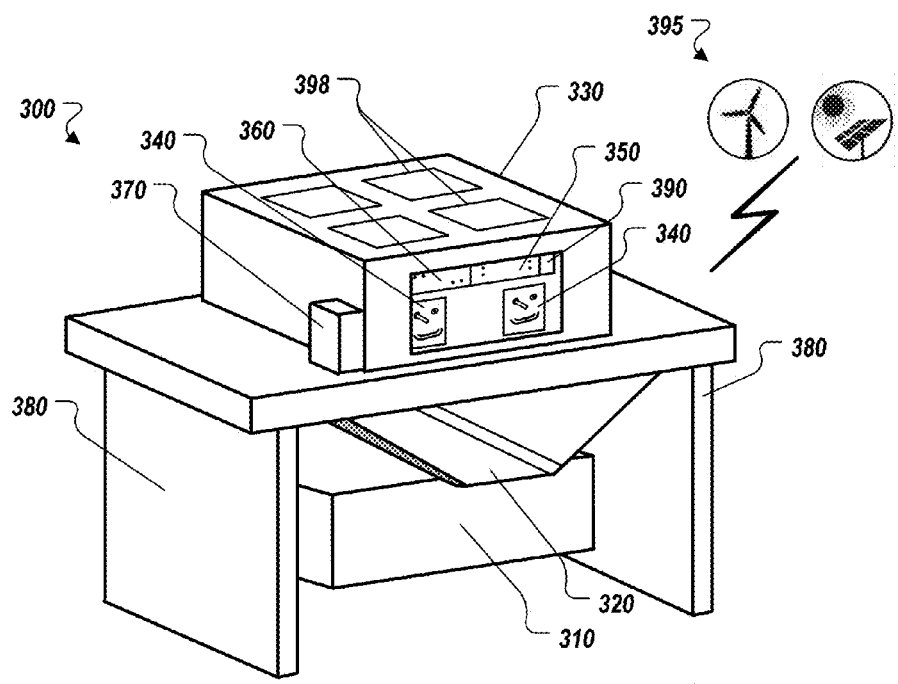
FIG. 3 shows an example of a substance analyzer unit configured and arranged to handle bulk materials delivered by conveyor belt.

FIG. 3 shows an example of a substance analyzer unit 300 configured and arranged to handle bulk materials delivered by conveyor belt. The bulk substance analyzer unit 300 includes an isotopic radioactive source of neutrons located within container 310, which includes material to condition and focus emitted neutrons that will pass up and through a channel 320. The channel 320 is an opening through which a conveyor belt can pass when the unit 300 is installed at a particular site, thus carrying the bulk substance to be analyzed past the neutron source 310. In addition, the unit 300 includes shielding 380 to reduce the neutron and gamma radiation going in undesirable directions. Shielding 380 is only shown on two sides of the unit 300, but once installed, the unit 300 can have shielding all around, including on the top and bottom of the unit 300. In addition, the unit 300 can also include structural support elements not shown in FIG. 3.

The bulk substance analyzer unit 300 also includes a detector box assembly 330, which includes inside two integrated detectors 340, a temperature-control module 350, and a detector interface communications module 360, such as described above. FIG. 3 shows the detector box assembly 330 with its access hatch removed to reveal one side of the housings for the two identical integrated detectors 340, with the temperature-control module 350 and the detector interface communications module 360 above them. In addition, an output interface 370 can be provided, which can be a wireless communications transceiver or a MAC unit for a local area network (e.g., an Ethernet switch).

In some implementations, the output interface 370 is integrated into the detector interface communications module 360. In some implementations, element 370 is a pull box that can be included to provide mechanical protection for a communications cable and a power cable. In some implementations, the detector interface communications module 360 is integrated into the electronics within an integrated detector 340.

As shown, the integrated detectors 340 can each have a handle for ease of installation in and removal from the detector box assembly 330. In addition, each integrated detector 340 can have a housing as described above with only two interfaces in the detector housing for receiving only two cables. A first of these two interfaces can be configured and arranged to receive a cable from the temperature-control module 350 for controlling a temperature of the detector, and a second of the two interfaces can be configured and arranged to receive a USB (Universal Serial Bus) cable from the detector interface communications module 360. In some implementations, the USB cable provides both a DC (direct current) voltage to power the electronics and a data line for the electronics to send and receive digital signals for the detector. Further, by using corrugated materials made from elements (e.g., carbon, hydrogen and oxygen) that contribute lower signals to background spectra when impacted by neutrons, signal to noise ratio has been improved beyond what has been previously achievable. By increasing the signal to noise ratio, the analyzer achieves better accuracy in a shorter time, which is significant for real-time applications and process control.

In some implementations, the bulk substance analyzer unit 300 includes a battery system 390 to receive power from a renewable energy source 395. Thus, the unit 300 can store extra power when made available by the renewable energy source 395 and continue to operate on battery power when the renewable energy source 395 is not providing power. In addition, the renewable energy source 395 can be integrated into the unit 300. For example, the unit 300 can have solar panels 398 or a windmill built on top of the detector box assembly 330 or shielding thereon.

In some implementations, the solar panels 398 can be oriented with respect to one or more of the shielding components 380 (or other similar components) so as to generate electrical power from gamma rays emanating therefrom. The solar panels 398 can be of a type that is tailored to generating power from gamma radiation. Thus, the neutron source 310 can become a source of power for the electronics in the unit 300. By designing the unit's electronics to reduce their power requirements, the energy of the extra neutrons generated by the source 310 (which energy would normally be wasted) can be used to produce gamma radiation that powers the panels 398 and thus the unit 300. In some implementations, all the electronics in the unit 300 are powered from such energy capture technology, and the unit 300 need not rely on any external source of energy, thereby becoming entirely self-sufficient. This can have significant advantages in remote locations where access to power and service capabilities are limited.

In some implementations, the distance between the neutron source 310 and the integrated detectors 340 is between six and twenty four inches. Other dimensions are also possible. PGNAA analyzers are typically large because of the need to shield neutron and gamma radiation for the safety of personnel that may work around an analyzer. The design of many analyzers also includes large amounts of material for conditioning the neutrons and focusing them into the material to be measured.

Figure 4:
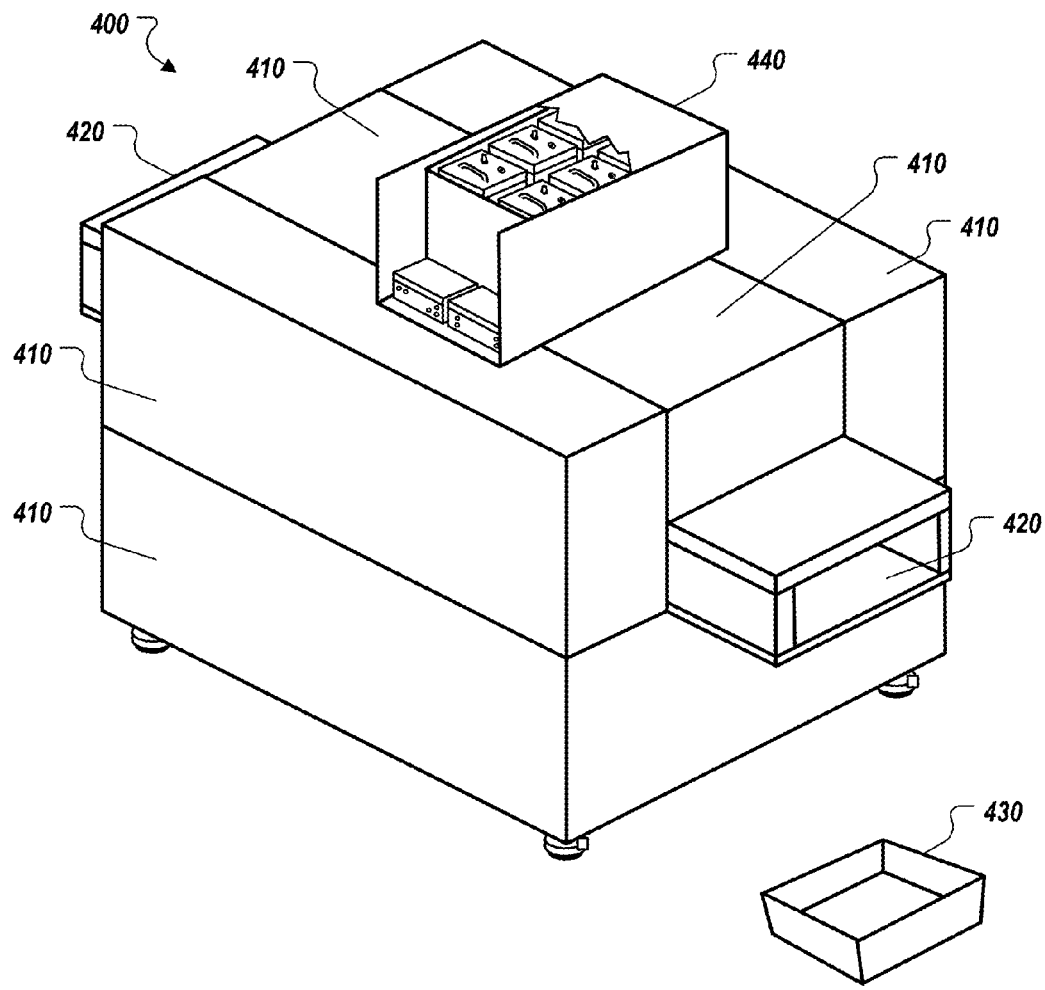
FIG. 4 shows an example of a substance analyzer unit configured and arranged to handle materials delivered in a container.

FIG. 4 shows an example of a substance analyzer unit 400 configured and arranged to handle materials delivered in a container 430. The unit 400 includes radiation shielding 410; as shown, the shielding 410 is modularized into pieces for ease of installation and maintenance. The unit 400 includes a detector assembly 440, which can include six integrated detectors, a temperature-control module, and a detector interface communications module. The integrated detectors can be similar to (or the same as) the integrated detectors 340, which each have a handle for ease for installation in and removal from the detector assembly 440, and also have a housing as described above with only two interfaces in the detector housing for receiving only two cables. This streamlined configuration simplifies installation and maintenance. The analyzer is put in place, the neutron source is installed, the power cable is connected, the Ethernet cable is plugged in, and the system begins to provide data.

In addition, the unit 400 includes a passage 420 sized to receive a container 430 from a first side of the passage 420 and eject the container 430 from a second side of the passage, or alternatively withdraw it from the first side. The container 430 holds the substance being analyzed and can be loaded by person or using automation (e.g., robots). Likewise, the container 430 can be passed through the passage 420 by person (with any appropriate tools) or using mechanization (e.g., on a train driven roller conveyor).

The analyzer unit 400 can be designed to measure the composition of low-density materials in a very short time as a means of receiving inspection of large loads of material, such as biomass, e.g., corn stover. The analyzer 400 can be designed to be installed at a receiving station where samples of loads of material can be inserted into the analyzer 400 on a continuous basis and provide firm analyses in a very short time, such as five minutes or less. The sample containers 430 can pass through the tunnel 420, residing in the measurement zone until the test is completed before exiting in one direction or the other. This allows the sample containers 430 to pass all the way through the analyzer in a continuous stream. In other implementations, opening 420 is only on one side of the unit 400, and each sample container 430 is inserted and extracted from that same side.

The substance loaded in each sample container 430 can be analyzed for determining the weight-per-cent of moisture, ash and of constituent elements of ash, as well as other elements. The calorific value of the sample can be calculated from the measured values.

Figure 5:
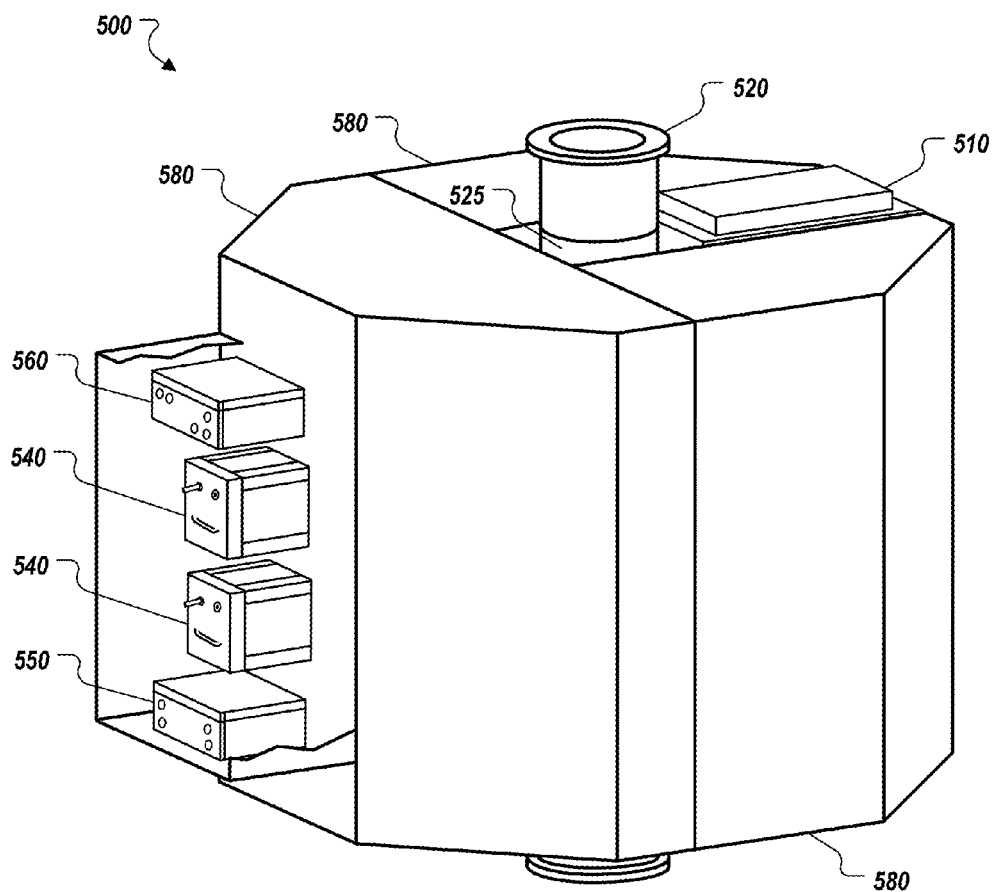
FIG. 5 shows an example of a substance analyzer unit configured and arranged to handle materials delivered in a slurry pipe.

FIG. 5 shows an example of a substance analyzer unit 500 configured and arranged to handle materials delivered in a slurry pipe 520. The slurry pipe 520 can be a main-stream slurry pipe, rather than an additional pipe that pulls samples from a main pipe. In order to readily surround the slurry pipe 520, the analyzer unit 500 can be composed of modularized units, as shown, that wrap around the pipe 520. In some implementations, the analyzer unit 500 is constructed as a clamshell type structure that readily opens and closes around the pipe 520. This can facilitate mounting the analyzer unit 500 around the pipe 520. In addition, the analyzer unit 500 can have a neutron source 510 (e.g., an isotopic neutron source) and shielding 580 built into the clamshell structure, as shown.

In addition, the pipe 520 can have a separate section 525 for the part of the pipe 520 that passes through the analyzer unit 500. The pipe section 525 can be made from a different material to reduce the background signal from the pipe, which can interfere with measurement accuracy. For example, the pipe section 525 can be made of a material that has a low neutron absorption cross-section (e.g., a macroscopic cross section of less than 0.008 per centimeter), such as high-density polyethylene or reactor-grade zirconium.

In some implementations, the analyzer unit 500 includes integrated detectors 540, a temperature-control module 550, and a detector interface communications module 560, such as described above. Note also that the detector assembly can be designed to receive two or more integrated detectors 540, thus allowing installation of an appropriate number of integrated detectors 540 within the analyzer unit 500 for a given application.

The analyzer unit 500 can be used with slurry pipes in various processes in many industries, such as fertilizer, nickel, iron, bauxite, or copper production. Slurry pipes can range from under 6 inches to more than 2 feet in diameter. In some implementations, the slurry pipe 520 has a diameter in the range of 8 to 12 inches. The analyzer unit 500 can provide an improved analysis system that can measure the full slurry stream on a continuous basis to obtain a true measurement of slurry composition without having to infer composition from measurement of a sample.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system with built-in memory. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results.

What is claimed is:

1. A detector unit for prompt gamma neutron activation analysis, the detector unit comprising:
   a scintillator configured to fluoresce when impacted by gamma rays generated by absorption of neutrons by a substance to be analyzed;
   a photosensor configured to receive fluorescence from the scintillator;

electronics coupled with the photosensor, the electronics configured to receive and process analog signals from the photosensor and output digital detection signals for the substance; and a housing containing the scintillator, the photosensor, and the electronics;

wherein the housing comprises interfaces configured to receive cables capable of providing power, temperature control, and digital communication signals.

2. The detector unit for prompt gamma neutron activation analysis of claim 1, wherein the interfaces are only two interfaces in the housing.

3. The detector unit for prompt gamma neutron activation analysis of claim 2, wherein one of the only two interfaces is a USB (Universal Serial Bus) interface configured to receive a USB cable to provide both the power and the digital communication signals.

4. The detector unit for prompt gamma neutron activation analysis of claim 1, comprising:

a source of high voltage coupled with the photosensor; and a pre-amplifier coupled with the photosensor;

wherein the electronics comprise an analog to digital converter (ADC) and a controller.

5. The detector unit for prompt gamma neutron activation analysis of claim 4, wherein the electronics comprise a communications module.

6. The detector unit for prompt gamma neutron activation analysis of claim 5, wherein the communications module comprises a wireless communications transceiver configured to send and receive digital data over a wireless network.

7. The detector unit for prompt gamma neutron activation analysis of claim 4, wherein the controller comprises a digital computer comprising:

a bus interface;

a hardware processor coupled with the bus interface;

memory coupled with the bus interface;

an input/output (I/O) interface coupled with the bus interface; and one or more expansion ports coupled with the bus interface.

8. The detector unit for prompt gamma neutron activation analysis of claim 1, wherein the housing comprises corrugated plastic configured and arranged to provide thermal insulation and mechanical support for the detector unit.

9. The detector unit for prompt gamma neutron activation analysis of claim 1, comprising a handle for ease of installation in and removal from a substance analyzer unit.

10. A substance analyzer unit comprising:

a source of neutrons;

an opening arranged with respect to the source of neutrons to receive a substance; and a detector assembly comprising integrated detector units, wherein each of the integrated detector units has a same size and comprises a scintillator configured to fluoresce when impacted by gamma rays generated by absorption of neutrons by the substance to be analyzed, a photosensor configured to receive fluorescence from the scintillator, electronics coupled with the photosensor and configured to receive and process analog signals from the photosensor and output digital detection signals for the substance, a housing containing the scintillator, the photosensor, and the electronics, wherein the housing comprises interfaces configured to receive cables capable of providing power, temperature control, and digital communication signals, and a handle for ease of installation in and removal from the detector assembly.

11. The substance analyzer unit of claim 10, wherein the detector assembly comprises:

a detector interface communications module coupled with each of the integrated detector units; and a temperature-control module coupled with each of the integrated detector units.

12. The substance analyzer unit of claim 11, wherein the temperature-control module is also a power-supply module that includes an AC (alternating current) power input interface and provides power to the detector interface communications module.

13. The substance analyzer unit of claim 11, wherein the interfaces are only two interfaces in the housing, and one of the only two interfaces is a USB (Universal Serial Bus) interface configured to receive a USB cable from the detector interface communications module to provide both the power and the digital communication signals.

14. The substance analyzer unit of claim 11, wherein the detector interface communications module includes interface ports for four or more integrated detector units and is configured to output digital data for the integrated detector units to a computer network.

15. The substance analyzer unit of claim 14, wherein the detector interface communications module comprises, or is coupled with, a wireless communications transceiver, and the computer network is a wireless network.

16. The substance analyzer unit of claim 10, wherein each of the integrated detector units comprises:

a source of high voltage coupled with the photosensor; and a pre-amplifier coupled with the photosensor;

wherein the electronics comprise an analog to digital converter (ADC) and a controller.

17. The substance analyzer unit of claim 16, wherein the electronics comprise a communications module.

18. The substance analyzer unit of claim 17, wherein the communications module comprises a wireless communications transceiver configured to send and receive digital data over a wireless network.

19. The substance analyzer unit of claim 16, wherein the controller comprises a digital computer comprising:

a bus interface;

a hardware processor coupled with the bus interface;

memory coupled with the bus interface;

an input/output (I/O) interface coupled with the bus interface; and one or more expansion ports coupled with the bus interface.

20. The substance analyzer unit of claim 10, wherein the housing comprises corrugated plastic configured and arranged to provide thermal insulation and mechanical support for the integrated detector unit.

21. A system comprising:

the substance analyzer unit of claim 10; and one or more additional substance analyzer units, each comprising a respective source of neutrons, opening, and detector assembly;

wherein the source of neutrons and the opening are arranged differently for each of the substance analyzer units; and wherein the detector assembly for each of the substance analyzer units is configured and arranged to receive the same size integrated detector units.

22. The system of claim 21, wherein:
a first of the substance analyzer units is configured and arranged to handle bulk materials delivered to the first substance analyzer unit by a conveyor belt; and
a second of the substance analyzer units is configured and arranged to handle materials delivered to the second substance analyzer unit in a slurry pipe.

23. The system of claim 21, wherein:
a first of the substance analyzer units is configured and arranged to handle bulk materials delivered to the first substance analyzer unit by a conveyor belt;
a second of the substance analyzer units is configured and arranged to handle materials delivered in a container that is inserted into the second substance analyzer unit; and
a third of the substance analyzer units is configured and arranged to handle materials delivered to the third substance analyzer unit in a slurry pipe.

* * * * *